US005554846A

United States Patent [19]
Regiec et al.

[11] Patent Number: 5,554,846
[45] Date of Patent: Sep. 10, 1996

[54] APPARATUS AND A METHOD FOR DETECTING ALARM MOLECULES IN AN AIR SAMPLE

[75] Inventors: Kenneth B. Regiec, Baltimore; Peter C. Stroosnyder, Finksburg; Stephen D. Kubicsko, Westminster; Charles H. Ward, II, Edgewood, all of Md.

[73] Assignee: Environmental Technologies Group, Inc., Baltimore, Md.

[21] Appl. No.: 509,387

[22] Filed: Jul. 31, 1995

[51] Int. Cl.$^6$ .................................................. H01J 49/04
[52] U.S. Cl. .......................... 250/288; 250/289; 250/287; 73/864.81; 73/31.02
[58] Field of Search .................................. 250/288, 289, 250/287; 73/864.81, 31.02

[56] References Cited

U.S. PATENT DOCUMENTS

| | | | |
|---|---|---|---|
| 4,317,995 | 3/1982 | Bradshaw et al. | 250/288 |
| 4,578,586 | 3/1986 | Preston | 250/382 |
| 4,943,929 | 7/1990 | Simonoff | 364/496 |
| 5,475,217 | 12/1995 | Bradshaw | 250/287 |

*Primary Examiner*—Jack I. Berman
*Attorney, Agent, or Firm*—Leonard Bloom

[57] ABSTRACT

In an apparatus for detecting alarm molecules, residual alarm molecules are automatically removed during a clear-down mode before a subsequent air sample is to be introduced. The apparatus comprises a detector unit, a sensor unit and a filtering sub-unit including a pump and a filter. During a challenge, the pump in the sub-unit is turned off, and the air sample passes from the inlet port of the first unit through the second unit to the output port of the first unit, thereby depositing alarm molecules in the first unit and the second unit. During the clear-down mode, the pump in the sub-unit is turned on, and outside air enters through the output port of the first unit, mixes with air flow from the output of the second unit, and passes through the sub-unit. Filtered air from the sub-unit exhausts the first unit through the inlet port of the first unit and passes into the second unit, thereby cleaning the first unit and the second unit from the alarm molecules deposited therein during the challenge mode.

14 Claims, 6 Drawing Sheets

APPARATUS AND A METHOD FOR DETECTING ALARM MOLECULES IN AN AIR SAMPLE

FIELD OF THE INVENTION

The present invention relates to a system for air analysis, and, more particularly, to chemical agent monitors (detectors) with automatic clear-down after a challenge.

BACKGROUND OF THE INVENTION

Chemical agent monitors are known to be used for detection of chemical warfare agents for battlefield, for environmental clean-up, for treaty monitoring and verification missions, and for other purposes, where harmful chemicals contained in the air (alarm molecules) are to be detected.

Mostly, the chemical agent monitors are Ion Mobility Spectrometry (IMS)-based apparatuses. For instance, known in the art, the Chemical Agent Monitor (CAM) is employed by several armies as a reliable system for the above-described purposes.

The Improved Chemical Agent Monitor (ICAM) maintains the performance characteristics of the CAMs but has an improved design which is more reliable and maintainable. As a hand-held surface monitor, the ICAM is unequaled; however, it monitors only one class of chemical at a time (nerve or blister), and it cannot be used as an unattended point detector.

Besides, after an ICAM detects alarm molecules, the residual alarm molecules must be removed before the unit is ready for a subsequent detection operation. The alarm molecule removal is referred to as a "clear-down." In order to remove the alarm molecules, the ICAM is provided with charcoal filter caps, which are manually positioned over the ICAM's inlet and exhaust parts to speed the clear-down. The charcoal filter removes residual alarm molecules from the exhausting air thereby producing clean air (or filtered air) which is directed to the ICAM's inlet port. The filtered air passes through the ICAM, displaces the remaining alarm molecules and, as a sequence, clears down the ICAM more rapidly.

Disadvantageously, this method of clearing the ICAM down involves manual involvement of an operator after each challenge, and therefore, is inconvenient and time and labor consuming.

It would be highly desirable to provide a chemical agent monitor with automatic clear-down after each challenge thereby avoiding an operator involvement.

SUMMARY OF THE INVENTION

It is, therefore, an object of the present invention to provide an apparatus and a method for detecting alarm molecules with automatic clear-down after a challenge.

It is another object of the present invention to provide an improved chemical agent monitor-detector, a duty cycle of which includes an alarm mode (or challenging mode) and a clear-down mode, and having a sub-unit automatically performing a filtering function only during a clear-down mode.

It is still another object of the present invention to provide an apparatus for an air analysis which would combine two units (an ICAM unit and a detector unit), so that the ICAM unit is nested and becomes a part of the detector unit, and such that a filtering sub-unit is accommodated within the detector unit.

The present invention finds its particular utility in an apparatus for monitoring and detecting alarm molecules in an air sample, wherein residual alarm molecules are to be removed before a subsequent air sample is to be introduced.

According to the teaching of the present invention, the apparatus comprises a first unit (an ICAM) and a second unit (a detector). An inlet port of the first unit is connected to an inlet port of the second unit, and an output port of the first unit is connected to an output port of the second unit. The inlet ports and the output ports of the first and the second units have access to the outside air.

The first unit accommodates a sub-unit comprising a pump and a filter, such that the inlet ports of the first unit and the second unit are connected to the output port of the sub-unit, and the output ports of the first unit and the second unit are connected to the inlet port of the sub-unit.

The duty cycle of the apparatus includes an alarm (or challenge) mode and a clear-down mode. During the alarm mode, the pump in the sub-unit is turned off, and the air sample passes from the inlet port of the first unit through the second unit to the output port of the first unit, thereby depositing alarm molecules in the first unit and the second unit. During the clear-down mode, the pump in the sub-unit is turned on, and outside air passes from the output port of the first unit, mixes with the air flow from the output of the second unit, and passes through the sub-unit. The filtered air exhausts through the inlet port of the first unit and enters the second unit, thereby cleaning the first unit and the second unit from the alarm molecules deposited therein during the alarm mode.

A pressure relief valve is nested between the output port of the first unit and the inlet port of the sub-unit to prevent an air flow through the sub-unit during the alarm mode.

During the clear-down mode, the filtered air from the output port of the sub-unit flows to the inlet ports of the first unit and the second unit. The air flow through the sub-unit is equal to the air flow through the second unit plus the air flow out of the inlet port of the first unit.

The second unit comprises a pump to move the air sample from the inlet port of the first unit through the second unit to the output port of the first unit during the alarm mode. In the clear-down mode, the pump in the second unit moves a part of the filtered air from the sub-unit through the second unit.

A method for detecting alarm molecules in an air sample according to the present invention comprises the steps of:

providing the apparatus of the present invention, during the alarm mode, turning off the pump in the sub-unit, such that the air sample passes from the inlet port of the first unit through the second unit to the output port of the first unit, thereby depositing alarm molecules in the first unit and the second unit, and during the clear-down mode, turning on the pump in the sub-unit, such that outside air passes into the output port of the first unit, mixes with an air flow from the output of the second unit, and passes through the sub-unit. Filtered air from the output of the sub-unit exhausts through the inlet port of the first unit and enters the inlet port of the second unit, thereby cleaning the alarm molecules deposited therein during the alarm mode from the first unit and the second unit.

These and other objects of the present invention will become apparent from a reading of the following specification taken in conjunction with the enclosed drawings.

DETAILED DESCRIPTION OF THE INVENTION

Figure 1:
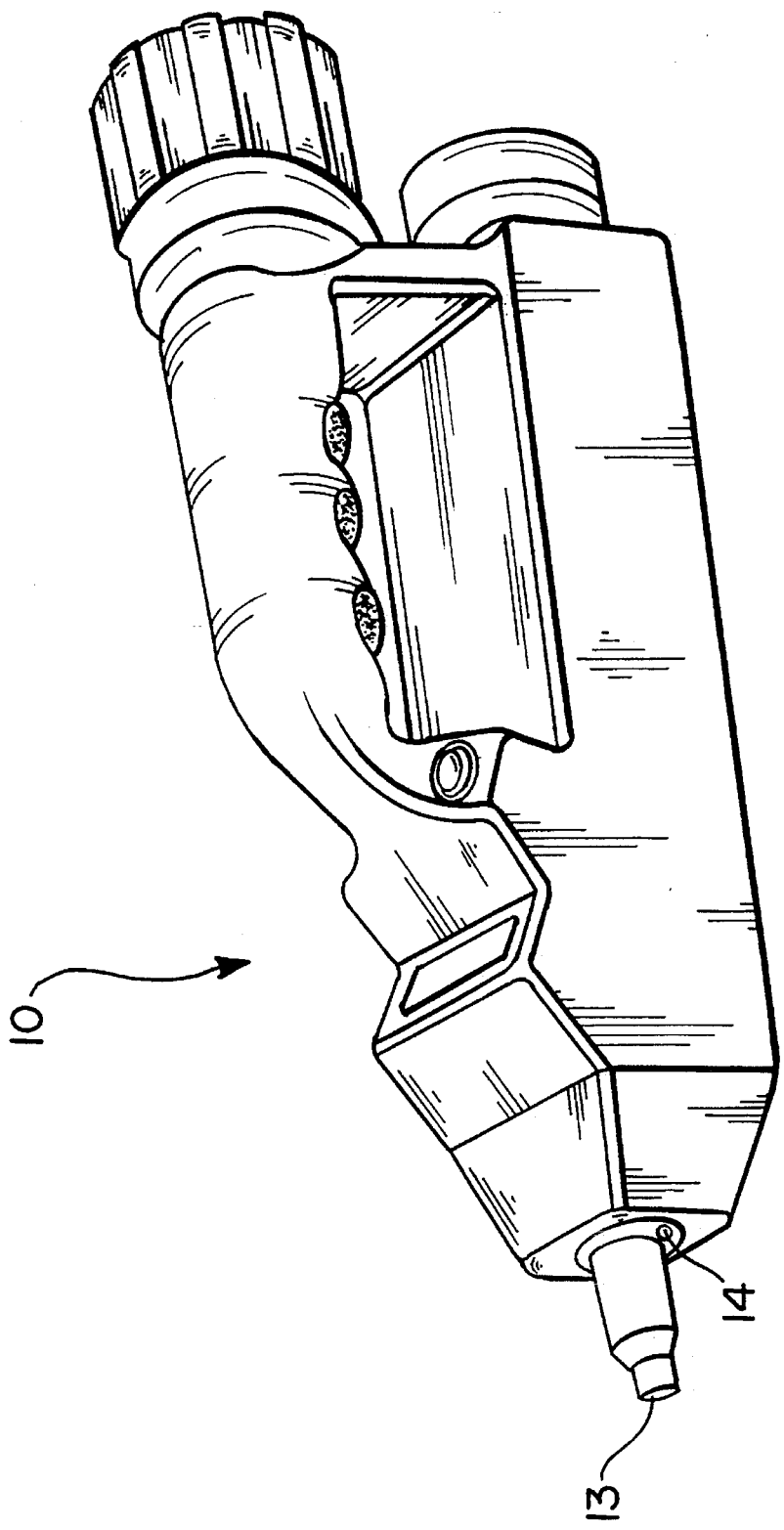
FIG. 1 is a perspective view of the Improved Chemical Agent Monitor (ICAM) of the prior art.
Figure 2:
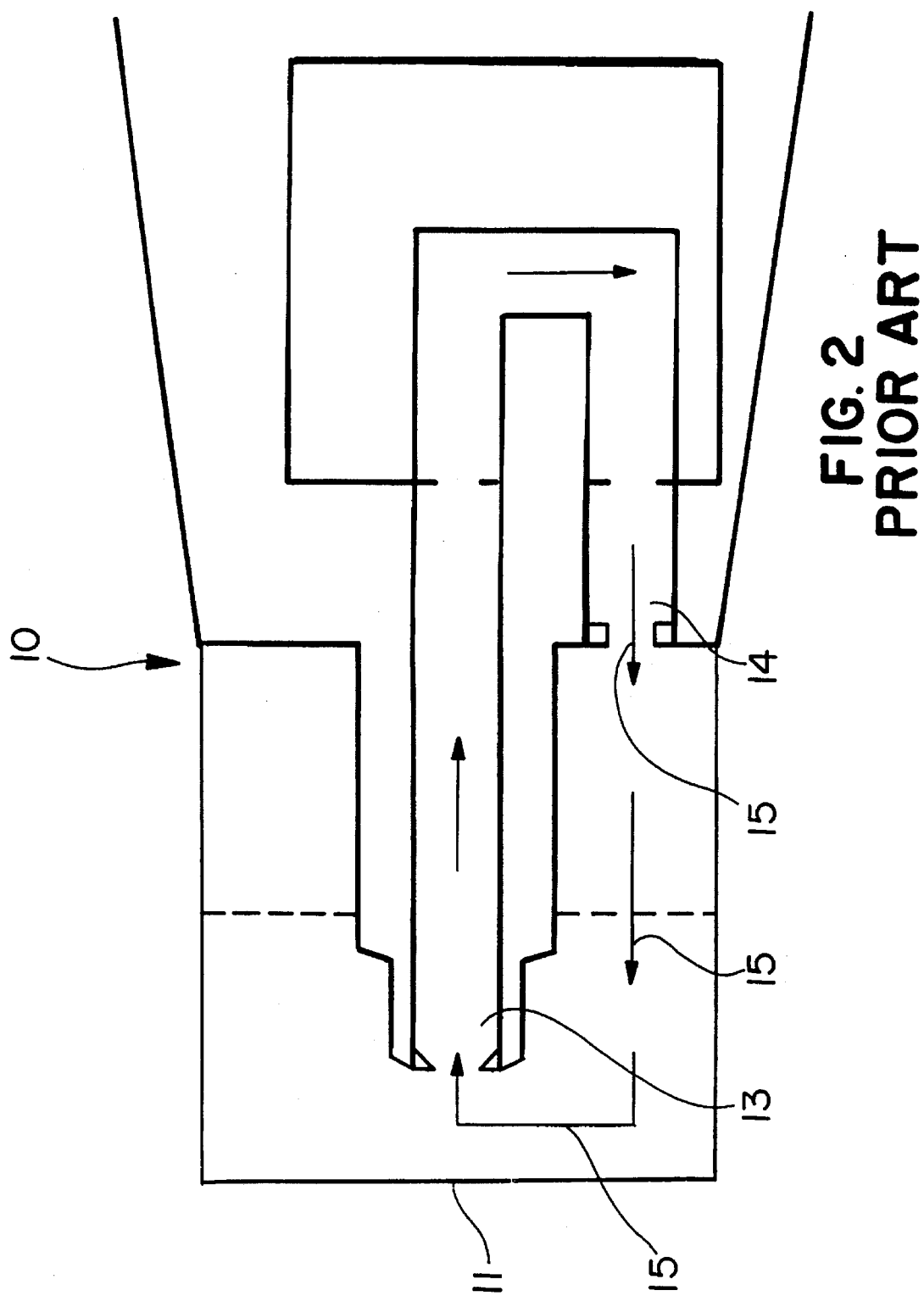
FIG. 2 shows somewhat schematically a longitudinal cross-section of the ICAM of the prior art.

Referring to FIGS. 1 and 2, the ICAM 10 is provided with charcoal filter cap 11, which is manually positioned over the ICAM's inlet 13 and exhaust ports 14 to speed the clear-down. The charcoal filter cap 11 removes residual alarm molecules from the exhausting air thereby producing clean air (or filtered air) which is directed to the ICAM's 10 inlet port 13. The filtered air 15 passes through the ICAM 10, displaces the remaining alarm molecules and, as a sequence, clears down the ICAM 10 more rapidly.

Figure 3:
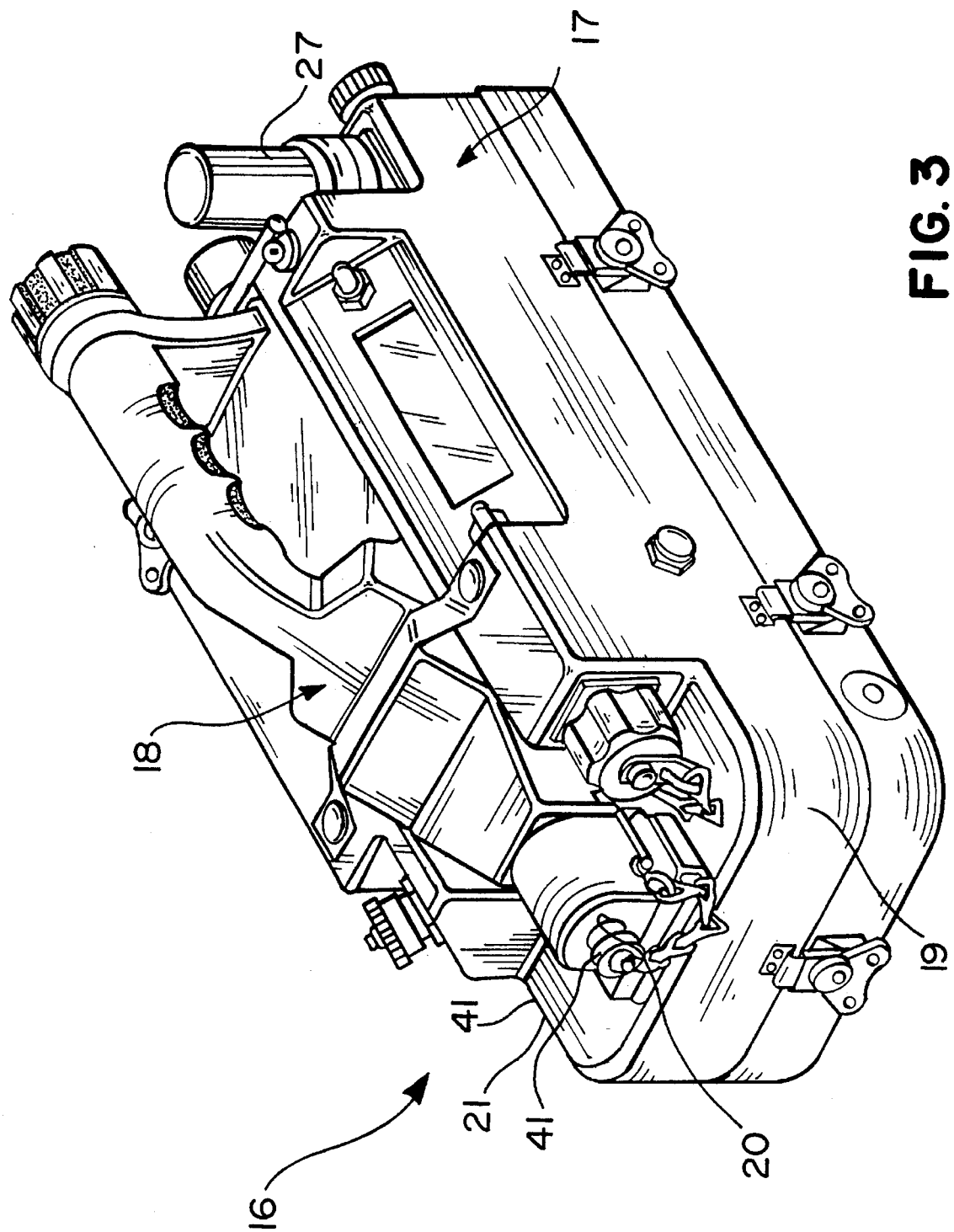
FIG. 3 is a perspective view of the Improved Chemical Agent Monitor-Detector (ICAM-D) of the present invention.
Figure 4:
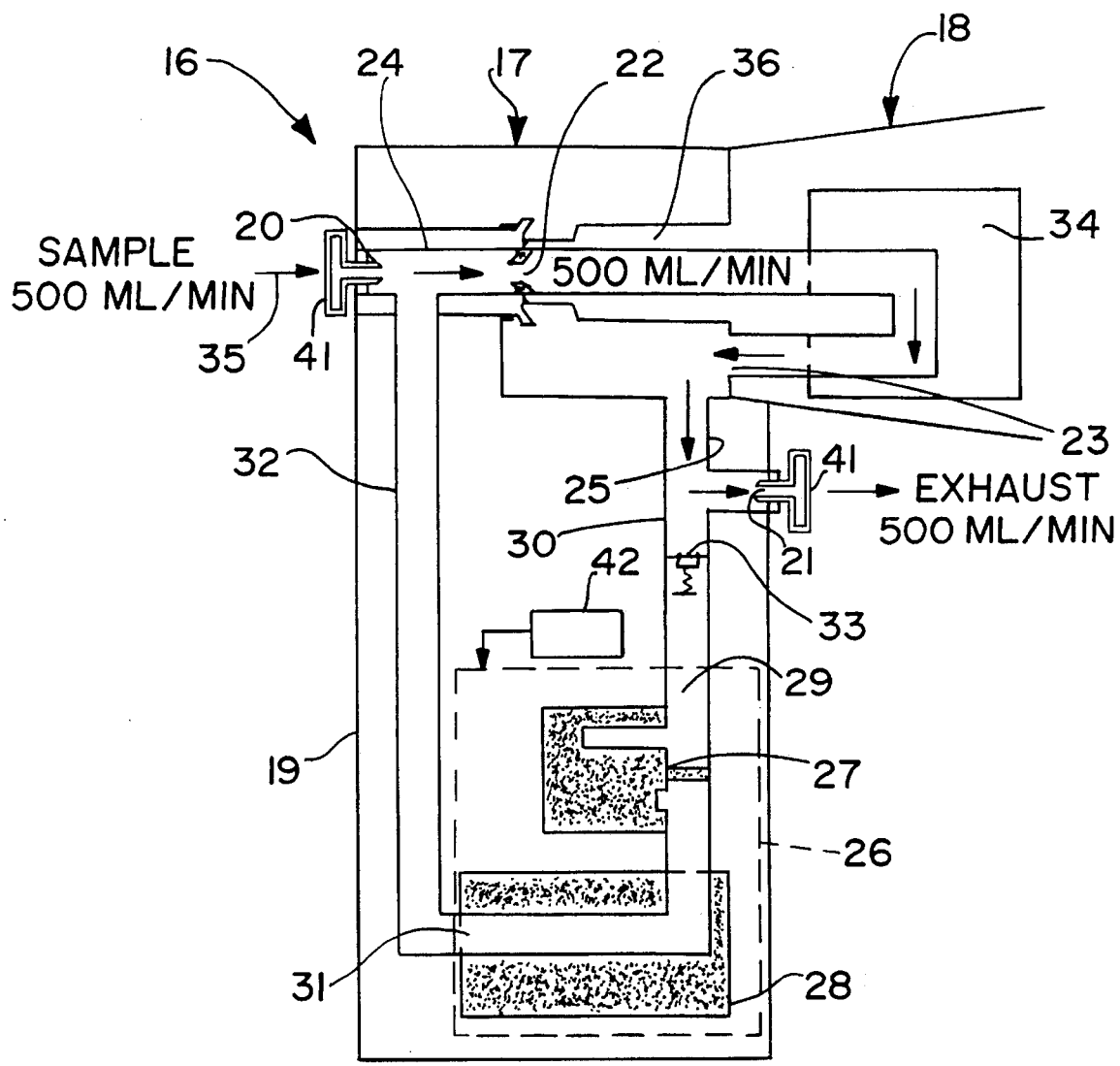
FIG. 4 is a longitudinal cross-section view of the ICAM-D of the present invention, showing air flow during a challenge (or alarm) mode of the duty cycle.
Figure 5:
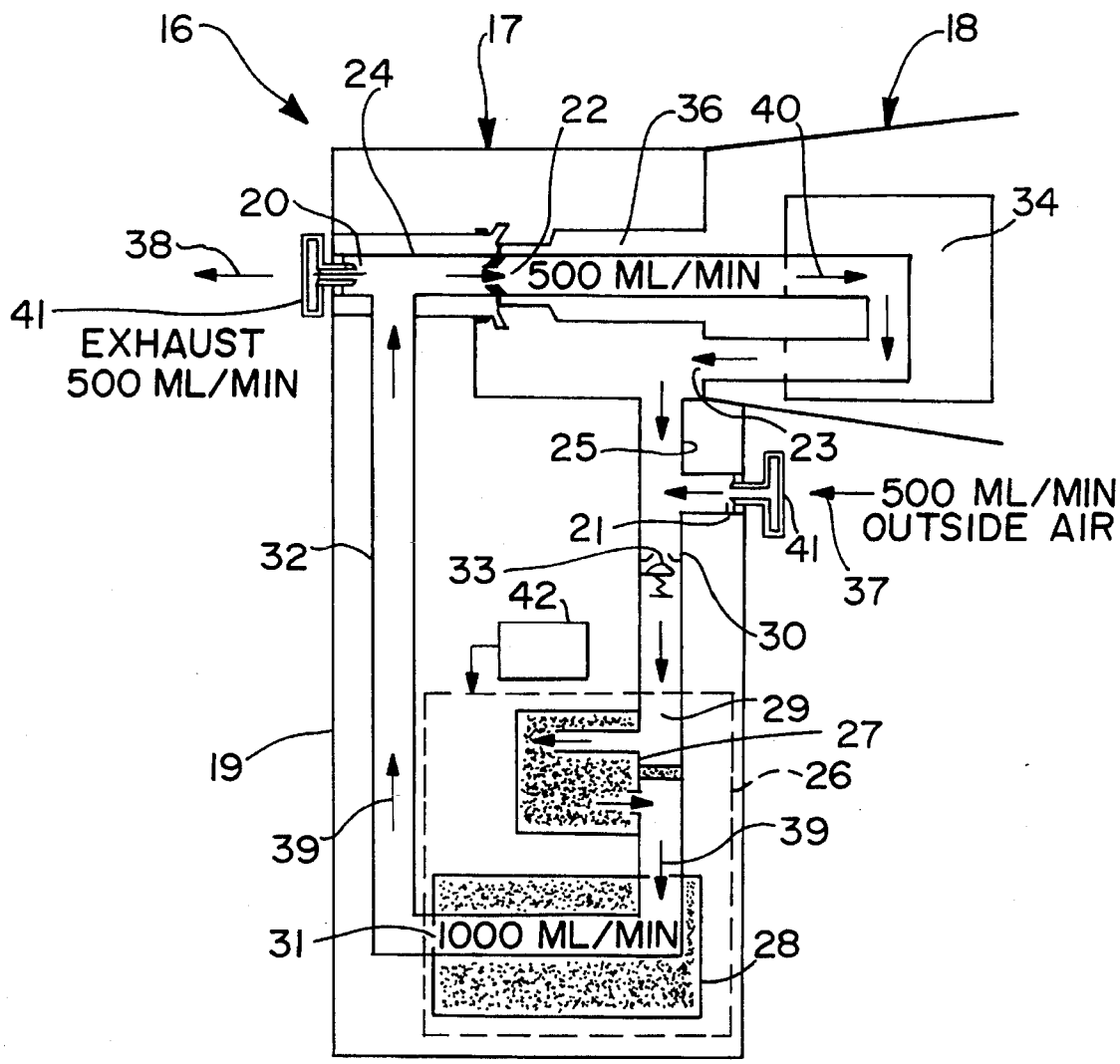
FIG. 5 is a longitudinal cross-section view of the ICAM-D of the present invention showing air flow during a clear-down mode of the duty cycle.
Figure 6:
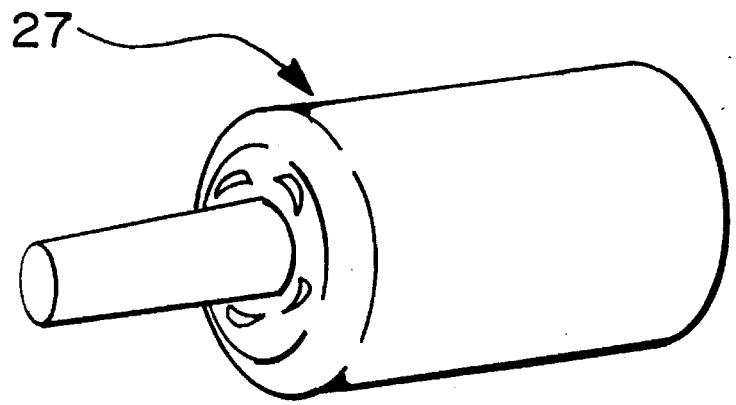
FIG. 6 shows schematically a charcoal filter employed in the present invention.
Figure 7:
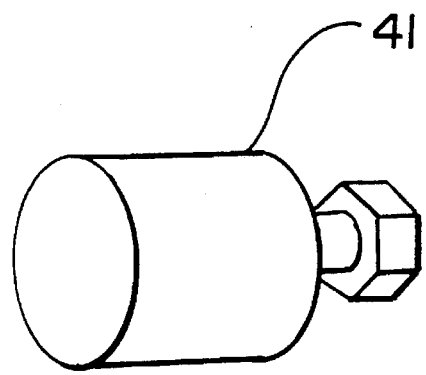
FIG. 7 shows schematically a dust/rain filter employed in the present invention.

Referring to FIGS. 3–7, the apparatus 16 for detecting alarm molecules in an air sample, further referred to as an Improved Chemical Agent Monitor-Detector (ICAM-D) 16, includes two units: a detector module 17 and a sensor module 18. As best shown in FIGS. 3, 4 and 5, the ICAM-D 16 incorporates the ICAM in order to provide stand-alone detection capability using the proven, type-classified ICAM as the core of the ICAM-D 16. The ICAM becomes the sensor module 18 for the ICAM-D 16, while the detector module 17 provides command and control functions. Both modules 17 and 18 have a common housing 19.

The ICAM makes use of the Ion Mobility Spectrometry (IMS) principles. The basic operation of IMS includes producing of ions and then separating and counting the different types of ions produced. In any IMS based system, several key subsystems and components control system performance. The incoming gas from the inlet permeates the membrane and enters the IMS drift tube. The drift tube houses the cell which consists of an ionizing chamber, an electronic gate, and an accelerator that terminates in an ion (or charge) collector. The ionization source is a radioactive foil plated with Nickel-63 (10 mC of Ni-63). In IMS, the ions travel a known distance along a drift tube, across which a potential gradient is applied. The drift tube acts as an accelerator. Ion groups with lighter mass accelerate more quickly and arrive at the collector first, while ion groups with greater mass arrive later in mass order. As each ion/ion cluster strikes the collector, it is represented as a peak in a collected current waveform. The relative position and magnitude of each peak carries information regarding the identity and concentration of the chemical(s) being detected. Each peak is assessed by a microprocessor system programmed with a detection Algorithm that recognizes peaks at specific locations. When a chemical is recognized, its presence and concentration is assessed against toxicity information stored in software memory, and the level is then indicated.

It will be appreciated by those skilled in the art, that, for the sake of simplicity of understanding the teachings of the present invention, FIGS. 4 and 5 show neither the cell for implementing the Ion Mobility Spectrometry, nor the software, electronics or electric circuitry associated with the IMS cell of the ICAM.

The detector module 17 has an inlet port 20 and an output port 21. The sensor (ICAM) module 18 has an inlet port 22 and an output port 23. The inlet port 20 is connected to the inlet port 22 by a passage 24, while the output port 21 is connected to the output port 23 by a passage 25, such that the ICAM (sensor module) 18 becomes an integral part of the ICAM-D 16. As best shown in FIGS. 4 and 5, the passage 24 is short, so that there will not be an alarm delay due to vapor transport or longer clear down due to increased surface area which would pick up alarm agent. The short passage 24 runs from the inlet 20 to the inlet 22 inside the ICAM-D housing which mates with the ICAM nozzle 36. The passage 25 is not critical and is longer than the passage 24. The passage 25 begins at the ICAM outlet 23 (located near the base of the inlet nozzle as shown in FIG. 3 (hidden). It continues on through the body of the ICAM-D 16, and finally connects to the output 21 on the a side of the ICAM-D 16.

The inlet 22 of the ICAM module 18 gathers the vapor to be analyzed and present the vapor to the membrane (not shown), which must permit vapors of alarm molecules to rapidly enter the cell while at the same time exclude as much moisture as possible.

The ICAM inlet 22 consists of a TEFLON® tube connected to the vacuum side of a pump 34. The tube outlet flares in a "wagon wheel" pattern to channel the vapor over the membrane. Vapors are then pulled through the pump 34 and exhausted to the atmosphere. An inlet heater (not shown) is used to ensure against alarm molecule hang-up on the TEFLON® surfaces.

A sub-unit 26 is nested in the detector module 17. The sub-unit 26 comprises a charcoal filter 27 (best shown in FIGS. 4–6) and a clear-down pump 28 (best shown in FIGS. 4, 5). The charcoal filter 27 is a two chambered cylindrical removable cartridge. The inlet and outlet are at the same end of the filter. The inlet tube is centered in the end of the filter. The outlet includes several slots in the end of the cylinder at the base of the inlet. The air flows into the center inlet and on through the first charcoal filled chamber. It then passes radially from center to circumference at the back end of the filter and then back down the outer charcoal filled chamber which surrounds the first chamber. It then passes through the outlet slots at the base of the inlet tube, emerging as cleaned air. The clean-down pump 28 is a dual diaphragm pump with two chambers. It has flapper type inlet and outlet valves. The reciprocating motion is provided by a scotch yoke which is driven by a 6 V DC motor.

An inlet port 29 of the sub-unit 26 is connected to output ports 21, 23 by a passage 30, while an output port 31 of the sub-unit 26 is connected by a passage 32 to the input ports 20 and 22.

A duty cycle of the ICAM-D 16 includes substantially two modes: a challenge (or alarm) mode and a clear-down mode. A pressure relief valve 33 is secured within the passage 30 between the inlet port 29 and output ports 21, 23. During the alarm mode operation the pressure in the passage 24 is lower than the pressure in the passage 25. The relief valve 33 is designed to just withstand this pressure difference so as to prevent the air flow through the sub unit 26. In the clear-down mode, the clear-down pump 28 of the sub unit 26 develops enough pressure to open the relief valve 33 permitting the air flow through the charcoal filter 27.

As best shown in FIG. 4, during the challenge, a pump 34 in the sensor (ICAM) module 18 is turned on (the clear-down pump 28 in the sub-unit 26 is turned off), and an air sample 35 enters the ICAM-D 16 from the outside through the inlet port 20, the passage 24, inlet port 22, nozzle 26 of the ICAM module 18 and the passage 25 and exits to the outside via output ports 21 and 23. No air flows through the turned-off pump 28. During the challenge, alarm molecules are deposited in the detector module 17, the sensor (ICAM) module 18, and the passages 24 and 25. The low pressure clear-down relief valve 33 prevents air flow through the sub-unit 26 during the challenge mode. It will be appreciated by those skilled in the art, that the low pressure relief valve can be placed in the input passage 30 and/or the output passage 32 of the sub-unit 26. A very dry air sample 35 is required in the ionizing chamber of the ICAM module 18. A pneumatic system is provided to supply the dry air, transport the incoming molecules to the ionizing source (not shown) in the ICAM module 18 and remove the modules from the ICAM module after discharge. The ICAM pneumatic system 20 includes the above-mentioned pump 34 and a sieve pack containing a molecular sieve.

The ICAM pump 34 is actually two individual pumps pneumatically separated but mechanically connected and driven by a common motor. One of the pumps draws the sample in the inlet 22 and the other pump supplies the internal airflow through the ICAM and sieve pack. The ICAM pump 34 is a proven pump that works exceptionally well with the other components.

The sieve pack provides important functions in the detection system that far exceed its minor function of being a receptacle for the molecular sieve that keeps the IMS cell dry and traps contaminants. In the ICAM, which uses a dopant chemistry to aid in interferant rejection and stabilize the IMC cell reference, the sieve pack also contains the dopant permeation tube.

The sieve pack contains a number of critical chambers that channel clean air to the IMS cell and receive polluted air from the IMS cell. It also serves as a mixing chamber for the dopant. The sieve pack also has a number of restrictors in various flow paths to control the relative pressure in the cell. Operating at a specific cell pressure is key to peak timing and algorithm recognition of the peaks.

The air flow entering the ICAM-D 16 via the inlet port 20, the air flow passing through the pump 34 and the air flow exhausting from the ICAM-D have the same mass-flow, for instance 500 ml/min.

After the alarm (or challenge), i.e., in the clear-down mode, the sub-unit 26 is activated, the clean-down pump 28 is turned on, the low pressure relief valve 33 opens in response to the decreased pressure of its output, and an outside air 37 (for instance, 500 ml/min.) enters via the output ports 21, 23 and a mass flow 38 exits via the inlet port 20. In the pump 28 activated mode, conservation of mass requires that the mass flow 39 through the sub-unit 26 is equal to the mass flow 40 through the ICAM module 18 plus the mass flow 38 out of the inlet port 20. The mass flow 38 is also equal to the flow 37 entering into the ICAM-D 16 via the output port 21. It is clear that, during the clear-down mode, the flow in the ICAM-D inlet 20 and output port 21 is reversed from the operation in the alarm mode. As best shown in FIG. 5, the mass flow 39 through the clear-down pump 28 is greater than the mass flow 40 through the ICAM module 18. All the ICAM outlet air 40 plus additional unfiltered outside air 37 from the outlet port 21 is drawn into the sub-unit 26. Filtered air flows out of the output port 31 of the sub-unit 26 to the inlet ports 20 and 22. An amount of the mass flow equal to the ICAM mass flow 40 goes to the input port 22 of the ICAM module 18, while the remaining mass flow 38 flows in the reverse direction out of the input port 20 of the ICAM-D 16. The clean air flowing out of the sub-unit, therefore, cleans down both the inlet port 20, the ICAM module 18, and the passages 24 and 25.

Dust/rain filters 41 (best shown in FIGS. 4, 5 and 7) cover the inlet port 20 and the output port 21 to protect the system from environmental interferences.

The ICAM-D 16 of the present invention, as described above, overcomes the limitations of the ICAM by providing the automatic clear-down of the whole system. The ICAM-D is very easy to use. From start to finish, the operator needs only to (1) place the ICAM sensor 18 into the detector module 17, (2) turn on the power and wait for 45 seconds while the detector module 17 performs a built-in self-test, and (3) verify proper function by challenging the detector module 17 with a chemical agent stimulant. Maximum recovery time from the alarm limit concentration to clear air is not more than 15 seconds. After an alarm, the detector immediately begins to clear down. After being reset, the detector immediately begins sampling the surrounding air. A full recovery occurs if no alarm molecules are detected for a period of 10 seconds.

As schematically shown in FIGS. 4 and 5, a controlling means 42 controls the operation of the ICAM-D 16. The detector module 17 contains a microprocessor which is responsible for the detailed timing and control in both the detector module 17 and the sensor module 18. The control details for challenge (or alarm mode) and for the clear-down mode have been discussed above. It will be appreciated by those skilled in the art, that specific circuits details for turning on and off the clean-down pump 28 do not include a new subject, and therefore have not been discussed in detail herein.

Both modules 17 and 18 are designed to be durable and reliable. The detector module 17 does not require preventive maintenance, since its built-up features will indicate when servicing is required. The ICAM-D is a self-contained system and devoid of expensive, heavy and bulky accessories.

Obviously, many modifications may be made without departing from the basic spirit of the present invention. Accordingly, it will be appreciated by those skilled in the art that within the scope of the appended claims, the invention may be practiced other than has been specifically described herein.

What is claimed is:

1. An apparatus for detecting alarm molecules in an air sample during an alarm mode, wherein residual alarm molecules are removed during a clear-down mode before a subsequent air sample is introduced, the apparatus comprising:

a first unit and a second unit, each of said first and second units having an inlet port and an output port, respectively, the inlet port of the first unit being connected to the inlet port of the second unit, the output port of the first unit being connected to the output port of the second unit, wherein the first unit includes a sub-unit comprising a pump and a filter, the sub-unit having an inlet port and an output port, wherein the inlet ports of the first unit and the second unit are connected to the output port of the sub-unit, wherein the output ports of the first unit and the second unit are connected to the inlet port of the sub-unit, wherein, during the alarm mode, the pump in the sub-unit is turned off, and the air sample passes from the inlet port of the first unit through the second unit to the output port of the first unit, thereby depositing alarm molecules in the first unit and the second unit, and wherein, during the clear-down mode, the pump in the sub-unit is turned on, outside air passes from the output port of the first unit and, being mixed with an air flow from the output port of the second unit, passes through the sub-unit, and exhausts the first unit through the inlet port of the first unit, and enters the inlet port of the second unit, thereby cleaning the first unit and the second unit from the alarm molecules deposited therein during the alarm mode.

2. The apparatus of claim 1, further including a pressure relief valve between the output port of the first unit and the inlet port of the sub-unit, the pressure relief valve preventing an air flow through the sub-unit during the alarm mode.

3. The apparatus of claim 1, further including means for connecting the respective inlet ports and output ports.

4. The apparatus of claim 1, wherein during the clear-down mode, the air flow out of the inlet port of the first unit is equal to the air flow into the output port of the first unit.

5. The apparatus of claim 1, wherein during the clear-down mode, an air flow from the output port of the sub-unit is filtered air, which flows to the inlet ports of the first unit and the second unit, and wherein the air flow through the sub-unit is equal to the air flow through the second unit plus the air flow out of the inlet port of the first unit.

6. The apparatus of claim 1, wherein said inlet port and said output port of the first unit and the second unit, respectively, have access to the outside air.

7. The apparatus of claim 1, wherein the second unit further comprises a means for causing the air sample to flow from the inlet port of the first unit through the second unit to the output port of the first unit.

8. In an apparatus detecting alarm molecules in an air sample during an alarm mode, a method for residual alarm molecules removal during a clear-down mode before a subsequent air sample is to be introduced, the method comprising the steps of:

providing a first unit and a second unit, each of said first and second units having an inlet port and an output port, respectively, connecting the inlet port of the first unit to the inlet port of the second unit, connecting the output port of the first unit to the output port of the second unit, providing the first unit with a sub-unit, the sub-unit comprising a pump and a filter, and the sub-unit having an inlet port and an output port, connecting the inlet ports of the first unit and the second unit to the output port of the sub-unit, connecting the output ports of the first unit and the second unit to the inlet port of the sub-unit, during the alarm mode, turning off the pump in the sub-unit, such that the air sample passes from the inlet port of the first unit through the second unit to the output port of the first unit, thereby depositing alarm molecules in the first unit and the second unit, and during the clear-down mode, turning on the pump in the sub-unit, such that outside air passes from the output port of the first unit, mixes with an air flow from the output port of the second unit, passes through the sub-unit, exhausts the first unit through the inlet port of the first unit, and enters the inlet port of the second unit, thereby cleaning the first unit and the second unit from the alarm molecules deposited therein during the alarm mode.

9. The method of claim 8, further including the step of providing a pressure relief valve between the output port of the first unit and the inlet port of the sub-unit, the pressure relief valve preventing an air flow through the sub-unit during the alarm mode.

10. The method of claim 8, further including the step of providing means for connecting the respective inlet ports and output ports.

11. The method of claim 8, wherein during the clear-down mode, the air flow out of the inlet port of the first unit is equal to the air flow into the output port of the first unit.

12. The method of claim 8, wherein during the clear-down mode, an air flow from the output port of the sub-unit is filtered air, which flows to the inlet ports of the first unit and the second unit, and wherein the air flow through the sub-unit is equal to the air flow through the second unit plus the air flow out of the inlet port of the first unit.

13. The method of claim 8, further including the step of providing said inlet port and said output port of the first unit and the second unit, respectively, with an access to the outside air.

14. The method of claim 8, further comprising the step of providing the second unit with a means for causing the air sample to flow from the inlet port of the first unit through the second unit to the output port of the first unit.

* * * * *